United States Patent [19]

Lederis et al.

[11] 4,385,050

[45] May 24, 1983

[54] ANTIHYPERTENSIVE POLYPEPTIDES

[75] Inventors: Karl Lederis, Calgary, Canada; David Stevenson, Scarsdale, N.Y.; Donald B. Olsen, Brewster, N.Y.; Charles D. Bossinger, White Plains, N.Y.; Everett Flanigan, Yorktown Heights, N.Y.

[73] Assignee: Armour Pharmaceutical Company, Tarrytown, N.Y.

[21] Appl. No.: 277,497

[22] Filed: Jun. 26, 1981

[51] Int. Cl.$^3$ .................. A61K 37/00; C07C 103/52
[52] U.S. Cl. .......................... 424/177; 260/112.5 R
[58] Field of Search ................ 424/177; 260/112.5 R

[56] References Cited

PUBLICATIONS

Chem. Abstr. 83, (1975) 108965w.
Chem. Abstr. 80, (1974) 57636t.
Chem. Abstr. 77, (1972) 56830c.
Chem. Abstr. 85, (1976) 117079d.
Chem. Abstr. 93, (1980) 199544d.
Biol. Abstr. 68, p. 62706.
Proc. Natl. Acad. Sci. 77, No. 8, pp. 5021–5024 (1980).

*Primary Examiner*—Delbert R. Phillips

[57] ABSTRACT

Peptides of the structure $R_1$—Ala—Arg—Ile—Glu—Asn—Glu—Glu—Glu—Gln—Ala—Gly—Leu—Asn—Arg—Lys—Tyr—Leu—Val—$R_2$ wherein $R_1$ is hydrogen, a peptide residue containing from 1 to 18 amino acid residues, or N-acyl, and $R_2$ is hydrogen, an alcohol moiety of an ester, an amide, or a peptide residue containing from 1 to 10 amino acid residues, wherein the acyl group is lower alkanoyl having from 1 to 8 carbon atoms, aroyl, or heterocarbonyl, and the alcohol moiety of the ester is an alkyl group having from 1 to 8 carbon atoms have antihypertensive activity.

4 Claims, No Drawings

ANTIHYPERTENSIVE POLYPEPTIDES

The acyl groups may be lower alkanoyl having from 1 to 8 carbon atoms, aroyl, or heterocarbonyl. The alkanoyl group may carry substituents such as hydroxy, amino, alkoxy, alkylamino, thio, alkylmercapto, and halogen, the alkyl in alkoxy, alkylamino, and alkylmercapto having from 1 to 8 carbon atoms. Suitable aroyl and heterocarbonyl groups include benzoyl, phenylacetyl, nicotinoyl, and the like. The benzoyl, phenylacetyl, and nicotinoyl groups may carry one or more substituents such as lower alkyl, lower alkenyl, lower alkynyl, hydroxy, lower alkoxy, hydroxylower alkyl, amino, lower alkylamino, amino-lower alkyl, thio, lower alkylmercapto, thio-lower alkyl, nitro, cyano, methylenedioxy, sulfonyl, sulfonamido, halo, and trifuloromethyl. The lower alkyl groups contain from 1 to 5 carbon atoms, and the lower alkenyl and lower alkynyl groups contain from 2 to 5 carbon atoms.

The alcohol moiety is preferably lower alkyl containing from 1 to 8 carbon atoms.

Preferably $R_2$ is hydrogen and $R_1$ is a peptide containing from 1 to about 18 amino acid residues and having the following structure wherein the bond to the core peptide is between Met 18 and Alanine.

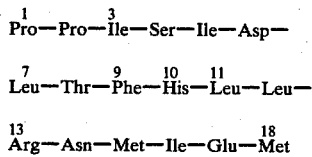

The invention will be more fully understood from the examples which follow. These examples are given by way of illustration and are not to be considered as limiting.

The procedures described in U.S. Pat. Nos. 3,915,949 and 4,055,524 were generally applied in the synthesis of the polypeptides of the present invention. In particular, the synthesis involved many reactions by which many new intermediate resin peptides were formed using a solid phase synthesis in which an insoluble polystyrene resin is chloromethylated with chloromethyl methyl ester to provide a product of the structure

wherein ⓡ is the insoluble polystyrene resin. The chloromethylated resin is then coupled with the first amino acid in the chain, then other amino acids in the prescribed sequence, using a system of protection and deprotection of the active amino and carboxyl groups. Following the coupling of the last amino acid in the chain, the resin is cleaved from the peptide chain and the remaining protecting groups removed.

Suitable protecting agents and the structures or atoms protected are as follows:

| Protected Group | Protecting Agents |
|---|---|
| Amino | t-butyloxycarbonyl (BOC) |
| Guanidine N (in Arg) | tosyl |
| Hydroxyl (in Ser and Thr) | benzyl |
| Carboxyl (in Asp and Glu) | benzyl |
| Indole N (in Trp) | formyl |
| Hydroxy (in Tyr) | 2-bromobenzyloxycarbonyl |
| ε-Amino (in Lys) | 2-chlorobenzyloxycarbonyl |
| Imidazole (in His) | benzyloxycarbonyl |

EXAMPLE 1

Deprotection

A 6.0 g sample of BOC-L-Valine resin (corresponding to 5.08 mmols Valine) was placed in the reaction vessel of a Vega Model 50 Peptide Synthesizer (Vega Biochemicals, Division of Vega Laboratories, Inc., P.O. Box 11648, Tucson, Ariz. 85734). The resin was washed four times, each for one minute, with 80 ml portions of toluene. The resin was next treated for one minute with 80 ml of 50% v/v redistilled trifluoroacetic acid in toluene, followed by a similar treatment for thirty minutes. After draining the resin, it was washed, each for one minute, with two 80 ml portions of toluene and then with four 80 ml portions of 10% v/v methanol in toluene. The resin was neutralized by treating, once for one minute and once for three minutes with two 80 ml portions consisting of five parts di-isopropylamine, ten parts methanol and eighty-five parts toluene (all v/v). Further washes were performed, for one minute each, with two 80 ml portions of methylene chloride. Total neutralization was ensured by treating for two minutes with 80 ml of 5% (v/v) di-isopropylamine in methylene chloride, followed by washes, each for one minute, with four 80 ml portions of methylene chloride.

Incorporation of Leucine (Residue 35)

To the deprotected L-Valine resin, with 5.08 meg of amine groups, was added the acylating solution, containing 10 mmols N (α)BOC-L-Leucine monohydrate (approximately 100% excess). This acylating solution was prepared by dissolving 2.5 g, 10 mmols BOC.-Leu.H₂O in 10 ml of M-1-hydroxybenzotrazole solution in dimethylformamide; to this was added toluene, 60 ml, and the resulting solution was cooled to 0°–5° C.; 5 ml 2 M N,N-dicyclohexylcarbodiimide solution in toluene was added. After washing the resin with two 80 ml portions of toluene, the acylating solution was added to the resin. Alternatively, the acylating solution is allowed to stand at room temperature for thirty minutes and then is added to the resin. The mixture was shaken overnight for convenience, although a coupling time as short as one hour would be adequate. The resin was drained and washed for one minute each time with two 80 ml portions of toluene, three 80 ml portions of methanol and four 80 ml portions of methylene chloride. A ninhydrin test (Kaiser et al, Anal. Biochem. 34, 595-8, (1969) was performed. On one occasion it was slightly positive and recoupling was carried out by adding to the drained resin a solution of 2.5 g BOC.Leu.H₂O dissolved in methylene chloride, 60 ml, plus dimethylformamide 10 ml followed by 5 ml of 2 N dicyclohexylcarbodiimide in toluene. After shaking for three hours, the resin was washed for one minute each with two 80 ml portions of methylene chloride and two 80 ml portions of toluene. The ninhydrin test was now negative.

This resin was deprotected as described above.

Incorporation of Tyrosine (Residue 34)

Tyrosine was incorporated as above except that 5.0 g (10 mmol) N(α)BOC-2-Bromobenzyloxycarbonyl-L-Tyrosine was dissolved in 10 ml M-1-hydroxybenzotriazole solution in dimethylformamide plus methylene chloride (not toluene) 60 ml.

This resin was deprotected as described previously.

Incorporation of the Remaining Residues 19-33 (inclusive)

Each of these residues were coupled similarly, but with occasional solvent changes or multiple couplings to give the desired

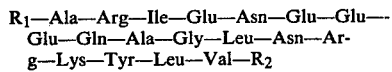
R₁—Ala—Arg—Ile—Glu—Asn—Glu—Glu—Glu—Gln—Ala—Gly—Leu—Asn—Arg—Lys—Tyr—Leu—Val—R₂ wherein both $R_1$ and $R_2$ are hydrogen. With regard to the solvent changes, starting with the addition of Asn and continuing with the addition of the remaining residues, dimethylformamide, rather than methylene chloride, was the preferred solvent in the first reactions. Deprotections were performed as described above.

EXAMPLE 2

A portion of the polypeptide made in Example 1 was further treated in the following manner.

Incorporation of Methionine (Residue 18)

This was coupled as previously described, using dimethylformamide as solvent. Deprotection was performed according to the following steps:

| | | |
|---|---|---|
| One treatment: | 80 ml | 50% v/v TFA in toluene, containing 0.1% v/v 2-mercaptoethanol (1 minute) |
| One treatment: | 80 ml | 50% v/v TFA in toluene, containing 0.1% v/v 2-mercaptoethanol (30 minutes) |
| Two treatments: | 80 ml | Toluene containing 0.1% v/v 2-mercaptoethanol (1 minute) |
| Four treatments: | 80 ml | 10% v/v methanol in toluene, containing 0.1% v/v 2-mercaptoethanol (1 minute each) |
| Two treatments: | 80 ml | 5:10:85 v/v di-isopropylamine:methanol:toluene containing 0.1% v/v 2-mercaptoethanol (1 × 1 minute, 1 × 3 minutes) |
| Two treatments: | 80 ml | 10% v/v methanol in toluene containing 0.1% v/v 2-mercaptoethanol (1 minute each) |
| Two treatments: | 80 ml | Methylene chloride (1 minute each) |
| One treatment: | 80 ml | 5% v/v di-isopropylamine in methylane chloride (2 minutes) |
| Four treatments: | 80 ml | Methylene chloride (1 minute each) |

Incorporation of Residues 17-11 (inclusive)

Each of these amino acids were coupled and subsequently deprotected as described for methionine (18).

Incorporation of Histidine (10)

After washing the drained deprotected resin with two 80 ml portions of dimethylformamide, a solution chilled to 0°-5° C. was added consisting of 7.0 g N(α)-BOC, N(im)-Z-L-Histidine containing benzene of crystallization, dissolved in 100 ml dimethylformamide. After shaking until a uniform suspension was obtained (approximately five seconds), 7.5 ml 2 M dicyclohexylcarbodiimide solution in toluene was introduced. After shaking overnight, the resin was washed successively with two 80 ml portions of dimethylformamide for one minute each, with one 80 ml portion of di-isopropylamine:methanol:toluene 5:10:85 (v/v) for five minutes, with three 80 ml portions of methanol and with four 80 ml portions of methylene chloride. Deprotection was performed as for methionine (18).

Incorporation of Residues 9-3 (inclusive)

Each of these amino acids were coupled and subsequently deprotected as described for methionine (18) except that after coupling, the washing procedure as described for histidine (10) was performed.

Incorporation of Residues 2 and 1

These were introduced simultaneously by using the protected dipeptide N(α)-BOC-L-Prolyl-L-Proline in the coupling reaction. This and the subsequent washes and deprotection were performed as for residues 9-3 (inclusive).

The compounds prepared in Example 1 and Example 2 possessed antihypertensive activity when tested according to the methods described in General and Comparative Endocrinology 24, 10-16 (1974), using the rat hind limb and in Pharmacology 18, 72-79 (1979), using the rat mesenteric artery strip. The compounds had activities of the order of (i) 0.01 to 0.025 units/mg in the rat hind limb test and (ii) 0.01 to 0.03 units/mg in the rat mesenteric artery strip test. The compounds would thus be useful in the treatment of hypertension in mammals. The compounds may be administered parenterally or by inhalation, and the physician will be competent to select the proper dosage and mode of administration.

I claim:

1. A compound of the structure

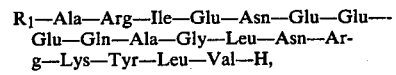
R₁—Ala—Arg—Ile—Glu—Asn—Glu—Glu—Glu—Gln—Ala—Gly—Leu—Asn—Arg—Lys—Tyr—Leu—Val—H, wherein $R_1$ is
 (a) Met,
 (b) Glu—Met,
 (c) Ile—Glu—Met,
 (d) Met—Ile—Glu—Met,
 (e) Asn—Met—Ile—Glu—Met,
 (f) Arg—Asn—Met—Ile—Glu—Met,
 (g) Leu—Arg—Asn—Met—Ile—Glu—Met,
 (h) Leu—Leu—Arg—Asn—Met—Ile—Glu—Met,
 (i) His—Leu—Leu—Arg—Asn—Met—Ile—Glu—Met,
 (j) Phe—His—Leu—Leu—Arg—Asn—Met—Ile—Glu—Met,
 (k) Thr—Phe—His—Leu—Leu—Arg—Asn—Met—Ile—Glu—Met,
 (l) Leu—Thr—Phe—His—Leu—Leu—Arg—Asn—Met—Ile—Glu—Met,
 (m) Asp—Leu—Thr—Phe—His—Leu—Leu—Arg—Asn—Met—Ile—Glu—Met,
 (n) Ile—Asp—Leu—Thr—Phe—His—Leu—Leu—Arg—Asn—Met—Ile—Glu—Met,
 (o) Ser—Ile—Asp—Leu—Thr—Phe—His—Leu—Leu—Arg—Asn—Met—Ile—Glu—Met, (p) Ile—Ser—Ile—Asp—Leu—Thr—Phe—His—Leu—Leu—Arg—Asn—Met—Ile—Glu—Met, (q) Pro—Ile—Ser—Ile—Asp—Leu—Thr—Phe—His—Leu—Leu—Arg—Asn—Met—Ile—Glu—Met, (r) Pro—Pro—Ile—Ser—Ile—Asp—Leu—Thr—Phe—His—Leu—Leu—Arg—Asn—Met—Ile—Glu—Met (s) or H.

2. A compound according to claim 1 wherein $R_1$ is hydrogen.

3. A compound according to claim 1 wherein $R_1$ is
Pro—Pro—Ile—Ser—Ile—Asp—Leu—Thr—Phe—His—Leu—Leu—Arg—Asn—Met—Ile—Glu—Met.

4. A method of treating hypertension which comprises the parenteral administration of a compound of claim 3 to a hypertensive mammal of an amount effective to reduce the blood pressure.

* * * * *